US010420836B2

(12) United States Patent
Skountzou et al.

(10) Patent No.: US 10,420,836 B2
(45) Date of Patent: Sep. 24, 2019

(54) METHODS OF IMMUNIZING A SUBJECT AND COMPOSITIONS RELATED THERETO

(71) Applicant: Emory University, Atlanta, GA (US)

(72) Inventors: Ioanna Skountzou, Atlanta, GA (US); Nicole Brock, McDonough, GA (US); Elena Vassilieva, Atlanta, GA (US); Richard Compans, Atlanta, GA (US)

(73) Assignee: Emory University, Atlanta, GA (US)

(*) Notice: Subject to any disclaimer, the term of this patent is extended or adjusted under 35 U.S.C. 154(b) by 14 days.

(21) Appl. No.: 15/289,705

(22) Filed: Oct. 10, 2016

(65) Prior Publication Data

US 2017/0100477 A1    Apr. 13, 2017

Related U.S. Application Data

(60) Provisional application No. 62/238,767, filed on Oct. 8, 2015.

(51) Int. Cl.
| | | |
|---|---|---|
| *A61K 39/39* | (2006.01) |
| *A61B 17/20* | (2006.01) |
| *A61K 39/145* | (2006.01) |
| *A61K 39/12* | (2006.01) |
| *A61K 9/00* | (2006.01) |
| *A61K 45/06* | (2006.01) |
| *A61K 47/22* | (2006.01) |
| *A61K 9/08* | (2006.01) |
| *A61K 31/015* | (2006.01) |
| *A61K 31/122* | (2006.01) |
| *A61K 31/167* | (2006.01) |
| *A61K 39/00* | (2006.01) |

(52) U.S. Cl.
CPC ........... *A61K 39/39* (2013.01); *A61B 17/205* (2013.01); *A61K 9/0021* (2013.01); *A61K 9/08* (2013.01); *A61K 31/015* (2013.01); *A61K 31/122* (2013.01); *A61K 31/167* (2013.01); *A61K 39/12* (2013.01); *A61K 45/06* (2013.01); *A61K 47/22* (2013.01); *A61K 2039/54* (2013.01); *A61K 2039/55511* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2002/0082527 A1 | 6/2002 | Liu | |
| 2008/0124322 A1 | 5/2008 | Foxwell | |
| 2008/0213461 A1 | 9/2008 | Gill | |
| 2008/0234258 A1* | 9/2008 | Baxter | C07D 309/08 |
| | | | 514/231.5 |
| 2009/0202492 A1 | 8/2009 | Beg | |
| 2010/0151000 A1 | 6/2010 | Thomas | |
| 2014/0170299 A1 | 6/2014 | Gill | |
| 2015/0174234 A1* | 6/2015 | Contorni | A61K 39/145 |
| | | | 424/209.1 |

FOREIGN PATENT DOCUMENTS

| | | |
|---|---|---|
| CN | 10255901 | 7/2012 |
| CN | 103495164 | 1/2014 |
| RU | 02184566 | 7/2002 |
| WO | 2011027222 | 3/2011 |

OTHER PUBLICATIONS

Gomez-Cabrero et al. (Plos One, Aug. 2013, p. 1-14).*
Bakry et al. (International Journal of Nanomedicine, 2007, p. 639-649).*
Amin et al. Alopecia areata: A review, Journal of the Saudi Society of Dermatology & Dermatologic Surgery (2013) 17, 37-45.
Kemeny et al. Dithranol: A Review of the Mechanism of Action in the Treatment of Psoriasis Vulgars, Skin Pharmacol, 1990, 3:1-20.
Koutsonanos et al. Transdermal Influenza Immunization with Vaccine-Coated Microneedle Arrays, PLoS One 4 (3): e4773, 2009.
Pulit-Penaloza et al. Modulation of influenza vaccine immune responses using an epidermal growth factor recepto kinase inhibitor, Sci Rep. 2015; 5: 12321.
Schopf et al. Immunosuppression by Anthralin, J Invest Dermat, 1996, 106(4) 841.
Skountzou et al. Transcutaneous immunization with inactivated influenza virus induces protective immune responses, Vaccine 24 (2006) 6110-6119.
Zhang et al. Endocytic mechanisms and toxicity of a functionalized fullerene in human cells, Toxicology Letters 191 (2009) 149-157.
Bunz et al. Effect of buckminsterfullerenes on cells of the innate and adaptive immune system: an in vitro study with human peripheral blood mononuclear cells, International Journal of Nanomedicine 2012, 7 4571-4580.
Chen et al. Antigenicity of fullerenes: Antibodies specific for fullerenes and their characteristics, Proc. Natl. Acad. Sci. USA vol. 95, pp. 10809-10813, 1998.

(Continued)

*Primary Examiner* — Agnieszka Boesen
(74) *Attorney, Agent, or Firm* — Emory Patent Group

(57) ABSTRACT

This disclosure relates to methods of immunization comprising administering an effective amount of an immunogenic composition comprising an antigen or vaccine and an adjuvant disclosed herein to a subject in need thereof. In certain embodiments, the adjuvant is 1,8-dihydroxy-9,10-dihydroanthracen-9-one or derivative thereof. In certain embodiments, the adjuvant is N-(3,5-bis-trifluoromethyl-phenyl)-5-chloro-2-hydroxy-benzamide or derivatives thereof. In certain embodiments, the adjuvant is a fullerene or derivatives thereof, e.g., Fullerene-$C_{60}$. In certain embodiments, the disclosure relates to compositions and devices comprising adjuvants disclosed herein.

14 Claims, 4 Drawing Sheets

(56) References Cited

OTHER PUBLICATIONS

Gomez et al. IMD-0354 Targets Breast Cancer Stem Cells: A Novel Approach for an Adjuvant to Chemotherapy to Prevent Multidrug Resistance in a Murine Model, PLoS One, 2013, 8(8): e73607.
Liu et al. The effect of Gd@C82(OH)22 nanoparticles on the release of Th1/Th2 cytokines and induction of TNF-a mediated cellular immunity, Biomaterials 30 (2009) 3934-3945.
Liu et al. Immunostimulatory properties and enhanced TNF-α mediated cellular immunity for tumor therapy by C60 (OH)20 nanoparticles, Nanotechnology 20 (2009) 415102 (10pp).
Nel et al. Toxic Potential of Materials at the Nanolevel, Science, 2006, 311 (5761), 622-627.
Raoof et al. Internalization of C60 fullerenes into cancer cells with accumulation in the nucleus via the nuclear pore complex.

\* cited by examiner

METHODS OF IMMUNIZING A SUBJECT AND COMPOSITIONS RELATED THERETO

CROSS REFERENCE TO RELATED APPLICATIONS

This application claims the benefit of priority to U.S. Provisional Application No. 62/238,767 filed Oct. 8, 2015. The entirety of this application is hereby incorporated by reference for all purposes.

BACKGROUND

Safety and tolerability concerns accompany the use of vaccines that incorporate live-attenuated or killed microorganisms. Vaccines containing virus particles incapable of replication are desired, e.g., virus-like particles that do not contain DNA or RNA but that are composed of pathogen derived proteins that can illicit an immune response. A drawback of this approach is that some protein-based vaccines lack some of the inherent immunostimulatory properties of whole organism-based vaccines resulting in suboptimal responses. Thus, there is a need to discover improved methods of vaccination.

Adjuvants are compounds typically co-injected with vaccines to boost immune responses. While certain adjuvants can enhance the immune response to some vaccines, they are not always universally effective or applicable to specific routes of immunization. Thus, there is a need to discover improved adjuvants depending on the antigen (vaccine) and route of immunization. For instance, vaccine responses against influenza are not greatly improved with the addition of alum. Alum, an adjuvant used in DTP vaccines, is a skin irritant and not suitable for skin vaccination. Therefore, there is a critical need to discover novel adjuvants that are broadly effective for each antigen and route of vaccination.

Skountzou et al. report transcutaneous immunization with inactivated influenza virus induces protective immune responses. Vaccine, 2006, 24, 6110-6119. See also Koutsonanos et al. Transdermal influenza immunization with vaccine-coated microneedle arrays. PloS one, 2009, 4, e4773. See also U.S. Patent Application Publication Nos 2014/0170299, 2008/0213461, and 2002/0082527.

Pulit-Penaloza et al. report modulation of influenza vaccine immune response using an epidermal growth factor receptor kinase inhibitor. Sci. Rep. 2015, 5, 12321.

Kermeny et al. report dithranol (Anthralin) is effective in the treatment of psoriasis that may exert an immunosuppressive effect. Skin Pharmacol, 1990, 3:1-20. See also Amin et al., J Saudi Soc Dermat & Dermat Surgery, 2013, 17, 37-45; Schopt et al., Immunosuppression by Anthralin, J Invest Dermat, 1996, 106(4) 841; and WO 2011/027222

Adenovirus vaccine utilizing IKK as an adjuvant is reported in US 2009/0202492. See also US 2010/0151000, US 2010/0151000, and US20080124322.

Zhang et al report endocytic mechanisms and toxicity of a functionalized fullerene in human cells. Toxicol Lett. 2009; 191(2-3):149-57. Vaccine adjuvant and vaccine formulations of fullerene derivatives are reported in CN103495164.

U.S. Patent Application Publication No. 2015/0174234 report influenza vaccines with oil-in-water emulsion adjuvants.

References cited herein are not an admission of prior art.

SUMMARY

This disclosure relates to methods of immunization comprising administering an effective amount of an immunogenic composition comprising an antigen or vaccine and an adjuvant disclosed herein to a subject in need thereof. In certain embodiments, the adjuvant is 1,8-dihydroxy-9,10-dihydroanthracen-9-one or derivative thereof. In certain embodiments, the adjuvant is N-(3,5-bis-trifluoromethyl-phenyl)-5-chloro-2-hydroxy-benzamide or derivatives thereof. In certain embodiments, the adjuvant is a fullerene or derivatives thereof, e.g., Fullerene-$C_{60}$. In certain embodiments, the adjuvant is IFN-λ and IP-10. In certain embodiments, the disclosure relates to compositions and devices comprising adjuvants disclosed herein.

In certain embodiments, the disclosure relates to the enhancement of vaccine efficacy and methods of dose sparing through the application of an adjuvant composition disclosed herein. In certain embodiments, the disclosure relates to methods of vaccinating against pathogens, such as influenza, by intramuscular, intradermal, subcutaneous, transdermal, transcutaneous, or epicutaneous administration of adjuvants disclosed herein in combination with a vaccine or antigen.

In certain embodiments, the antigen comprises a polypeptide sequence of a pathogen. In certain embodiments, the antigen is monovalent or multivalent. In certain embodiments, the pathogen is a virus, bacterium, or fungus. In certain embodiments, the antigen is a virus particle, viral envelope protein, an influenza hemagglutinin or neuraminidase. In certain embodiments, the vaccine is a live, attenuated, or killed virus.

In certain embodiments, the disclosure relates to immunogenic compositions comprising an antigen or vaccine and an adjuvant disclosed herein. In certain embodiments, the antigen comprises a polypeptide sequence derived from a pathogen. In certain embodiments, the pathogen is a virus, bacteria, or fungus. In certain embodiments, the antigen is a virus particle, viral envelope protein, an influenza hemagglutinin or neuraminidase. In certain embodiments, the vaccine is a live, attenuated, or killed virus.

In certain embodiments, the disclosure contemplates intradermal delivery devices comprising a composition disclosed herein. In certain embodiments, the intradermal delivery device is a needle comprising a hollow housing, wherein the adjuvant is contained within the hollow housing. In certain embodiments, the intradermal delivery device is a needle comprising a biodegradable polymer or non-biodegradable solid, wherein the adjuvant is contained within the biodegradable solid or coated on the needle. In certain embodiments, the intradermal delivery device is a needle with a diameter of less than one hundred micrometers or one millimeter or a shaft length of less than one hundred micrometers or one millimeter. In certain embodiments, the microneedle length is 100-700 microns. In certain embodiments, intradermal delivery devices is an insulin syringe and the needle length is between 4-12 mm. In certain embodiments, the needle is configured with an adaptor that prevents the needle from penetrating the skin not more than one millimeter or not more than one hundred micrometers.

DETAILED DISCUSSION

Figure 1A:
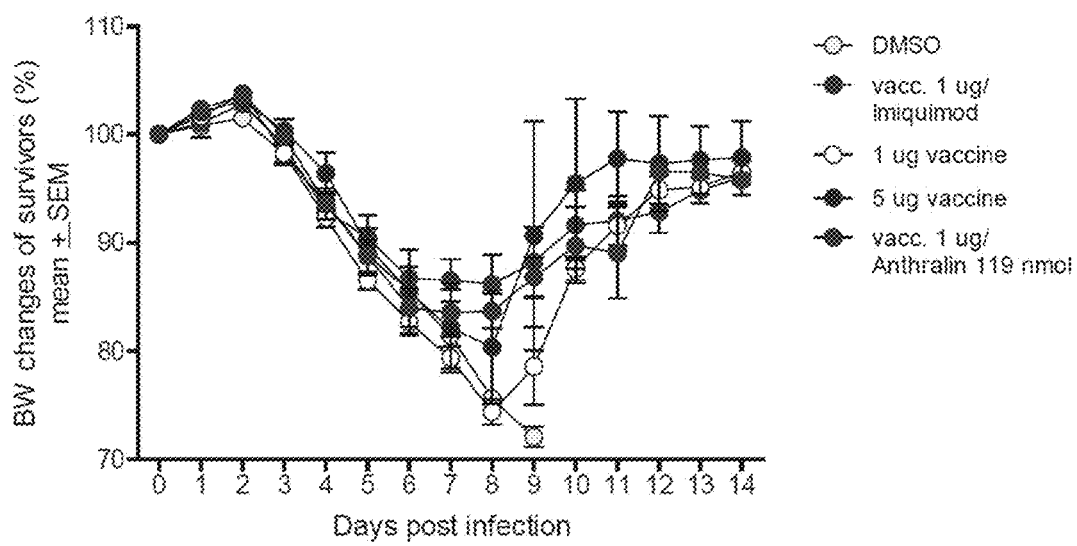
FIG. 1A shows data on body weight changes of mice vaccinated with a single dose of 1 μg HA A/Victoria/210/2009 subunit influenza vaccine after intranasal challenge with A/Udorn/72 (4×LD50). DMSO: naïve mice received DMSO only which is the solvent for anthralin (dithranol); imiquimod: TLR7, ligand mixed with vaccine and used as a positive control; Anthralin: candidate adjuvant mixed with vaccine.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin of beta-propiolactone), sonication, radiation, heat or any other conventional means sufficient to prevent replication or growth of the organism while maintaining its immunogenicity.

As used herein, the term "immune response" refers to a response elicited in an animal. An immune response may refer to cellular immunity (CMI); humoral immunity or may involve both. As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise an inactivated toxin (toxoid) or antitoxin.

As used herein, the term "multivalent" means a vaccine containing more than one antigen whether from the same species (i.e., different isolates of FMD virus serotypes), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants are strongly immunogenic in their own right and are believed to function synergistically.

An "effective amount" of an immunogenic composition, e.g. as used in a vaccine of the disclosure refers to an amount sufficient to show a meaningful benefit in a subject being treated, when administered as part of a vaccination dosing regimen. Those of ordinary skill in the art will appreciate that, in some embodiments, a particular composition may be considered to contain a prophylactically or therapeutically effective amount if it contains an amount appropriate for a unit dosage form administered in a specific dosing regimen, even though such amount may be insufficient to achieve the meaningful benefit if administered as a single unit dose. Those of ordinary skill will further appreciate that an effective amount of an immunogenic composition may differ for different subjects receiving the composition, for example depending on such factors as the desired biological endpoint, the nature of the composition, the route of administration, the health, size and/or age of the subject being treated, etc. In some embodiments, an effective amount is one that has been correlated with beneficial effect when administered as part of a particular dosing regimen, e.g. a single administration or a series of administrations such as in a "boosting" regimen.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. The derivative may be a prodrug. Derivatives may be prepared by any variety of synthetic methods or appropriate adaptations presented in synthetic or organic chemistry textbooks, such as those in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Adjuvants

Figure 1B:
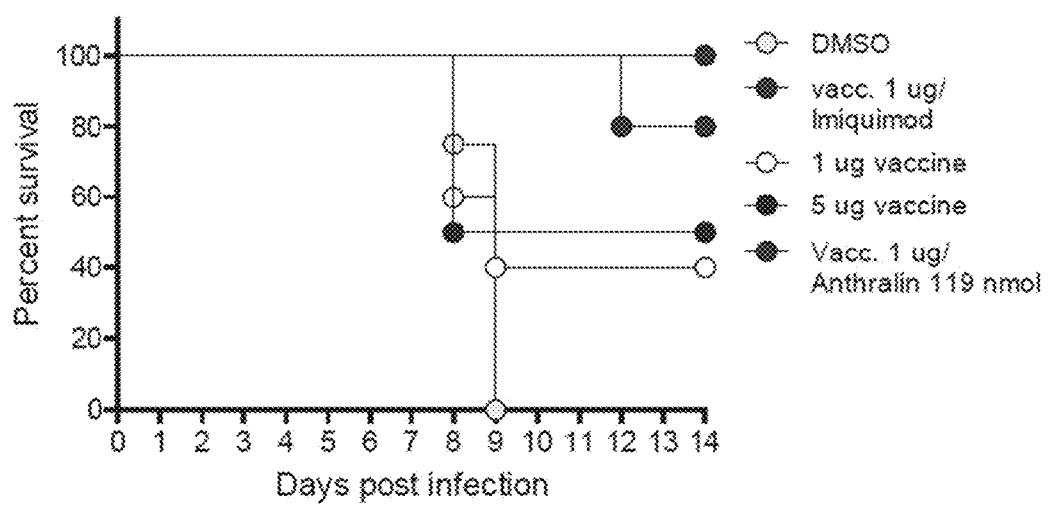
FIG. 1B shows data on survival rates of mice vaccinated with a single dose of 1 μg HA A/Victoria/210/2009 subunit influenza vaccine after intranasal challenge with A/Udorn/72 (4×LD50). DMSO: naïve mice received DMSO only which is the solvent for anthralin; imiquimod: TLR7, ligand mixed with vaccine and used as a positive control; Anthralin; candidate adjuvant mixed with vaccine.
Figure 2A:
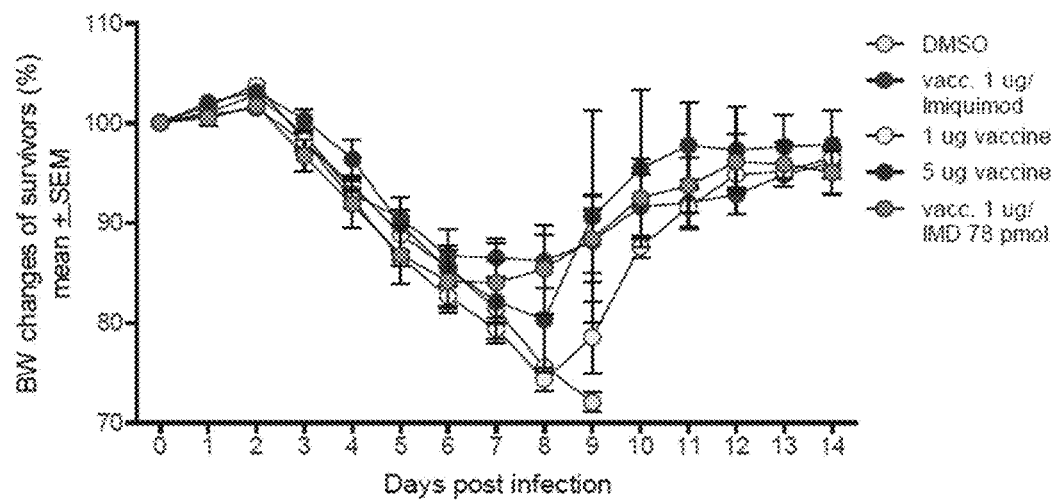
FIG. 2A shows data on body weight changes of mice vaccinated with a single dose of 1 μg HA A/Victoria/210/2009 subunit influenza vaccine after intranasal challenge with A/Udorn/72 (4×LD50). DMSO: naïve unvaccinated mice received DMSO only which is the solvent for IMD 0354; imiquimod: TLR7, ligand mixed with vaccine and used as a positive control; IMD 0354; candidate adjuvant mixed with vaccine.
Figure 2B:
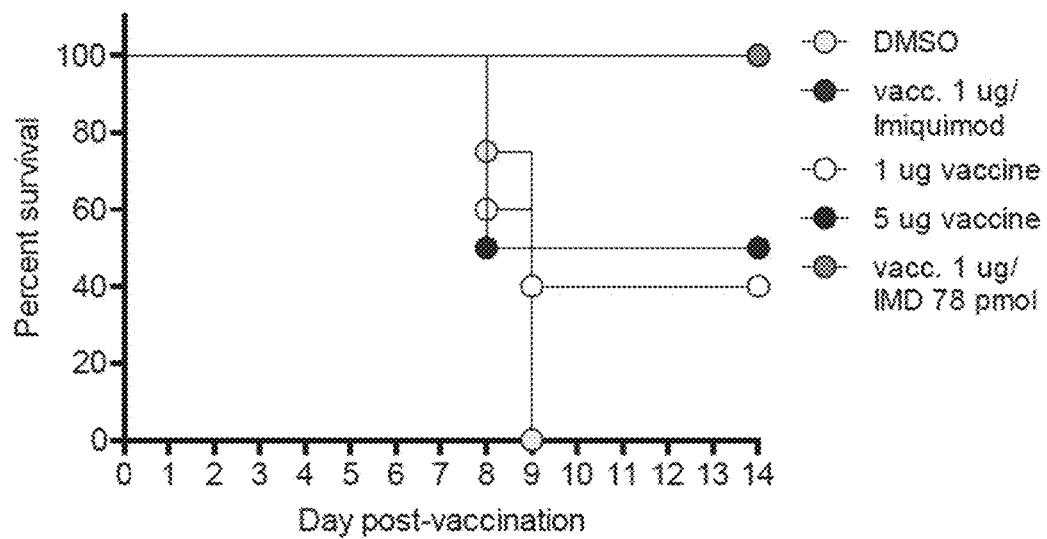
FIG. 2B shows data on survival rates of mice vaccinated with a single dose of 1 μg HA A/Victoria/210/2009 subunit influenza vaccine after intranasal challenge with A/Udorn/72 (4×LD50). DMSO: naïve unvaccinated mice received DMSO only which is the solvent for IMD 0354; imiquimod: TLR7, ligand mixed with vaccine and used as a positive control; IMD 0354; candidate adjuvant mixed with vaccine.
Figure 2C:
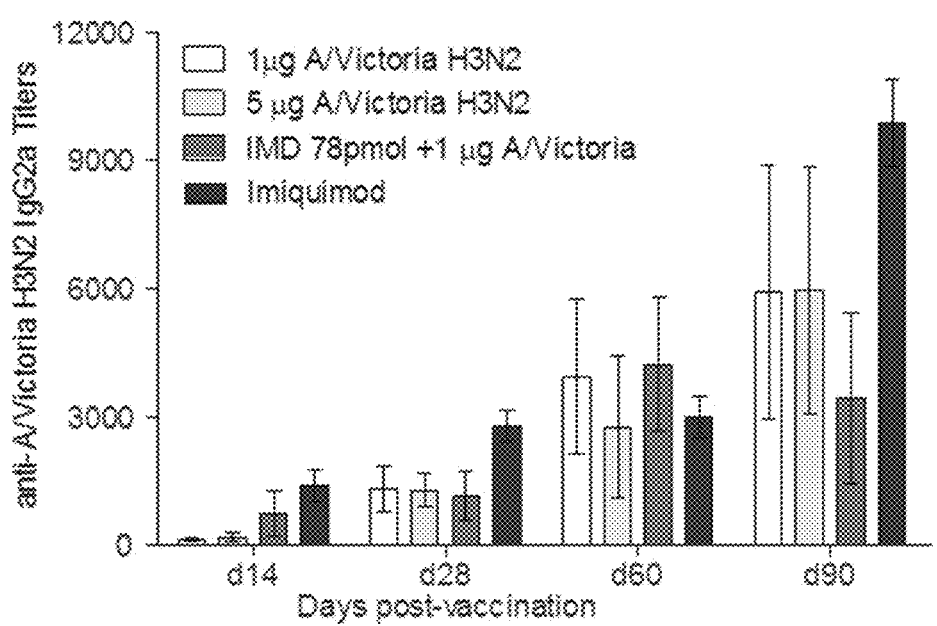
FIG. 2C shows data on the antibody titers in serum from mice vaccinated with a single dose of 1 μg HA A/Victoria/210/2009 subunit influenza vaccine. DMSO: naïve unvaccinated mice received DMSO only which is the solvent for IMD 0354; imiquimod: TLR7, ligand mixed with vaccine and used as a positive control; IMD 0354; candidate adjuvant mixed with vaccine.

To address the need for novel skin adjuvants, several agents were discovered to be effective as adjuvants for skin immunization. One identified adjuvant is anthralin. See Lowe et al. Anthralin for psoriasis: short-contact anthralin therapy compared with topical steroid and conventional anthralin. Journal of the American Academy of Dermatology 10, 69-72 (1984). It induces apoptosis of keratinocytes and activates cell death pathways, triggering pro-inflammatory responses leading to cytokine secretion and immune cell recruitment in the skin. Application of anthralin to mouse skin and human skin cells up-regulated gene expression for several pro-inflammatory cytokines. See Lange et al., Anthralin stimulates keratinocyte-derived proinflammatory cytokines via generation of reactive oxygen species. Inflammation research: official journal of the European Histamine Research Society, 47, 174-181 (1998). Anthralin can generate reactive oxygen species (ROS) and these molecules activate NFκB and epidermal growth factor (EGF) activation in keratinocytes. Peus et al. Antipsoriatic drug anthralin induces EGF receptor phosphorylation in keratinocytes: requirement for $H_2O_2$ generation. Experimental dermatology 13, 78-85 (2004). Despite numerous data exploring the mechanisms of anthralin in skin, there has not been one definitive mechanism of action. The ability of anthralin to induce high cell death in keratinocytes, leads to the possibility of death receptor activation in neighboring cells or infiltrating immune cells, triggering protective immune responses when used as an adjuvant for vaccination. In some cases, anthralin may be immunosuppressive but overall, the mechanisms of anthralin are not completely understood. There are no data on the use of anthralin as an adjuvant for skin immunization. Experiments disclosed herein indicate that when anthralin is used as an adjuvant for intradermal influenza vaccination, it induces protective immune responses (FIG. 1).

Another identified adjuvant is IMD 0354. IMD 0354 (N-(3,5-bis-trifluoromethyl-phenyl)-5-chloro-2-hydroxybenzamide) is a salicylamide compound that inhibits Iκbα phosphorylation by inhibiting IKKβ (IKK2). The rationale behind selecting IMD 0354 as a skin adjuvant was based on a study that generated a mouse model lacking IKKβ only in the epidermis. See Pasparakis et al. TNF-mediated inflammatory skin disease in mice with epidermis-specific deletion of IKK2. Nature 417, 861-866 (2002). In this model, the pro-inflammatory molecules TNF-α and IL-1β were highly induced in skin, despite the lack of NFκB signaling. NF-κB is important in the maintenance and immune responses generated in keratinocytes, the main cell type in the epidermis. Lack of IKKβ did not alter the integrity of the keratinocytes. There was an increase in IL-1β but most likely triggered by TNF-α from the dermis. In this model, the dermis produced key chemokines (MIP-1, MIP-2, IP-10 and MIG) important for immune cell recruitment and activation. There are studies that show IMD 0354 as immunosuppressive, such as those reported by Tanaka et al., Topical application with a new NF-kappaB inhibitor improves atopic dermatitis in NC/NgaTnd mice. The Journal of investigative dermatology 127, 855-863, (2007). The authors suggested that topical treatment of atopic dermatitis with IMD 0354 in a mouse model reduced infiltration and proliferation of CD4 T cells, mast cells, and eosinophils, and had a localized suppressive effect on IL-4, IL-5, IL-12 gene expression in skin, but there were no differences in cytokine gene expression in draining lymph nodes or on serum antibody titers.

Fullerene was also identified as adjuvant for skin immunization. Fullerene is a spherical nanoparticle molecule made of 60 carbon atoms in a closed-cage structure. Fullerene can interact with cells, activating cell signaling pathways and triggering phagosome formation. Cadenas et al., Buckyballs (fullerenes): free radical sponges or inflammatory agents? Archives of toxicology 86, 1807-1808, (2012). Several studies suggest that binding of nanoparticles to proteins may define their interaction with cells and tissues in vivo. Marano et al. Nanoparticles: molecular targets and cell signaling. Archives of toxicology 85, 733-741, (2011). It has been proposed that nanoparticles can induce mitogen-activated kinases (MAPK) and other transcription factors (NFκB, AP1, Nrf2), pathways for initiating immune responses. Fullerene can recruit cells following skin immunization. See Haniffa et al. Human skin dendritic cells in health and disease. J Dermatol Sci 77, 85-92, (2015) and Horohov et al. Characterization of the in situ immunological responses to vaccine adjuvants. Veterinary immunology and immunopathology 164, 24-29, (2015).

Figure 3A:
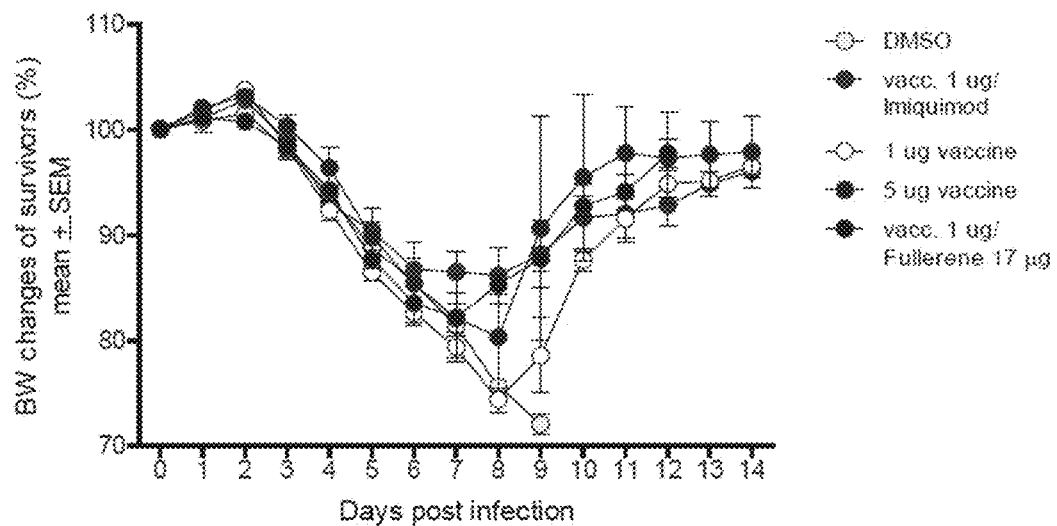
FIG. 3A shows data on body weight changes of mice vaccinated with a single dose of 1 μg HA A/Victoria/210/2009 subunit influenza vaccine after intranasal challenge with A/Udorn/72 (4×LD50). DMSO: naïve unvaccinated mice received DMSO only; imiquimod: TLR7, ligand mixed with vaccine and used as a positive control; Fullerene, candidate adjuvant mixed with vaccine (in PBS).
Figure 3B:
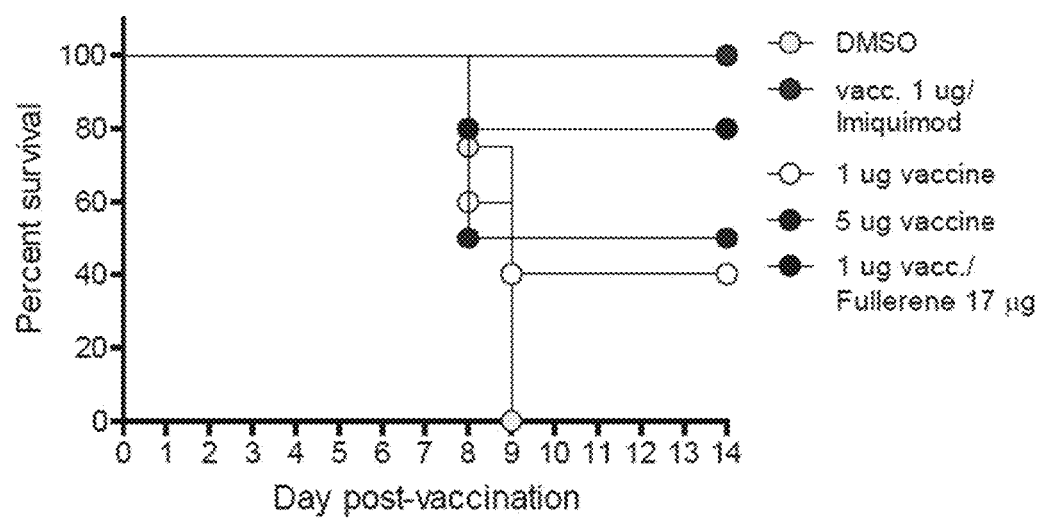
FIG. 3B shows data on survival rates of mice vaccinated with a single dose of 1 μg HA A/Victoria/210/2009 subunit influenza vaccine after intranasal challenge with A/Udorn/72 (4×LD50). DMSO: naïve unvaccinated mice received DMSO only; imiquimod: TLR7, ligand mixed with vaccine and used as a positive control; Fullerene, candidate adjuvant mixed with vaccine (in PBS).

Experiments herein indicate that fullerene (non-modified pristine C60) is an ideal adjuvant for skin immunization as when co-administered with influenza vaccine, improved protective immune responses that increased survival after virus challenge (FIG. 3). A potential mechanism for fullerene as an adjuvant for skin immunization is modification of vaccine internalization pathways in skin antigen presentation cells (APCs). See Liu et al. The roles of direct recognition by animal lectins in antiviral immunity and viral pathogenesis. Molecules 20, 2272-2295, (2015) and Nestle et al. Skin immune sentinels in health and disease. Nat Rev Immunol 9, 679-691 (2009).

This modification may improve antigen presentation resulting in protective immunity. A derivative of fullerene was shown to rely on cholesterol-dependent endocytosis for uptake by keratinocytes and required ATP. See Manoury. Proteases: essential actors in processing antigens and intracellular toll-like receptors. Frontiers in immunology 4, 299, (2013). Fullerene is considered as nanoparticle due to its structure that can recruit cells following skin immunization. The toxicity of fullerenes has been reported in Zhang et al., Endocytic mechanisms and toxicity of a functionalized fullerene in human cells. Toxicology letters 191, 149-157, (2009). At the low doses used for skin vaccination, no adverse effects were seen four months post-adjuvanted vaccination. Vaccine adjuvant and vaccine formulations of fullerene derivatives are reported in CN103495164.

The present disclosure relates to the enhancement of vaccine efficacy/dose sparing through the application of a vaccine adjuvant. In certain embodiments, the disclosure relates to a methods of vaccinating against diseases, such as influenza, by a method of intramuscular, intradermal, subcutaneous, transdermal, transcutaneous, or epicutaneous administration of adjuvants disclosed herein with vaccines.

In certain embodiments, the adjuvant is anthralin (1,8-dihydroxy-9,10-dihydroanthracen-9-one) or dithranol which is an anthracene derivative (hydroxyanthrone). Anthralin is used as a treatment for psoriasis, a skin disease caused by epidermal hyperproliferation and keratosis and for the treatment of alopecia, an autoimmune disease leading to hair loss. Anthralin is of interest as an adjuvant for skin vaccination due to induction of multiple signaling pathways in the skin. Anthralin can generate reactive oxygen species (ROS) and these molecules activate NFkB transcription factors and epidermal growth factor (EGF). Anthralin triggers cytokine and chemokine release from skin cells leading to immune activation.

In certain embodiments, the adjuvant is IMD 0354 (N-(3,5-bis-trifluoromethyl-phenyl)-5-chloro-2-hydroxy-benzamide) or derivatives thereof. IMD 0354 is of interest as a skin adjuvant due to a study showing that inhibition of IKK in the mouse epidermis led to an inflammatory disease, thus triggering an immune response.

The Influenza Virus Vaccines and Antigens

Compositions and methods of the instant disclosure contemplate the inclusion or use of an influenza virus vaccine or antigen.

In certain embodiments, the adjuvant compositions disclosed herein comprise antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the disclosure may include the step of mixing antigens from more than one influenza strain. A trivalent vaccine is preferred, which includes, antigens from two influenza A virus strains and one influenza B virus strain. Trivalent vaccines can benefit from adjuvants because H3N2 vaccine strains are less immunogenic, and the virus strain is more virulent. In some embodiments of the disclosure, the compositions may include antigen from a single influenza A strain. In some embodiments, the compositions may include antigen from two influenza A strains, provided that these two strains are not H1N1 and H3N2. In some embodiments, the compositions may include antigen from more than two influenza A strains.

In certain embodiments, the adjuvant compositions disclosed herein comprise influenza virions but, as an alternative, antigens such as hemagglutinin can be expressed in a recombinant host (e.g. in an insect cell line using a baculovirus vector) and used in purified form. The antigen may take the form of a live virus or, more preferably, an inactivated virus. Chemical means for inactivating a virus include treatment with an effective amount of one or more of the following agents: detergents, formaldehyde, formalin, beta-propiolactone, or UV light. Where an inactivated virus is used, the vaccine may comprise whole virion, split virion, or purified surface antigens (including hemagglutinin and, usually, also including neuraminidase). Virions can be harvested from virus-containing fluids by various methods. For example, a purification process may involve zonal centrifugation using a linear sucrose gradient solution that includes detergent to disrupt the virions.

In certain embodiments, the adjuvant compositions disclosed herein comprise split virions. Split virions are obtained by treating virions with detergents (e.g., ethyl ether, polysorhate 80, deoxycholate, tri-N-butyl phosphate, Triton X-100, Triton N101, cetyltrimethylaintrionium bromide, Tergitol NP9, etc.) to produce subvirion preparations, including the 'Tween-ether' splitting process. Splitting of the virus is typically carried out by disrupting or fragmenting whole virus, whether infectious or non-infectious with a disrupting concentration of a splitting agent. The disruption, results in a full or partial solubilization of the virus proteins, altering the integrity of the virus. Preferred splitting agents are non-ionic and ionic (e.g. cationic) surfactants e.g. alkylglycosides, alkylthioglyeosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanois (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Split virions can be resuspended in sodium phosphate-buffered isotonic sodium chloride solution.

In certain embodiments, the adjuvant compositions disclosed herein comprise influenza antigens presented in the form of virosomes as nucleic acid free viral-like liposomal particles.

In certain embodiments, the adjuvant compositions disclosed herein comprise seasonal attenuated influenza virus strains, i.e., vaccines change from season to season. For example, the vaccine includes two influenza A strains (H1N1 and H3N2) and one influenza B strain.

In certain embodiments, the adjuvant compositions disclosed herein comprise attenuated viruses from pandemic strains (i.e. strains to which the vaccine recipient and the general human population are immunologically nave), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the vaccine may protect against one or more of influenza A virus HA subtypes H1, H2, H3, H4, H5, H6, H7, H8, H9, H10, H11, H12, H13, H14, H15 or H16. The adjuvant composition may protect against one or more of influenza A virus NA subtypes N1, N2, N3N4, N5, N6, N7, N8 or N9.

In certain embodiments, the adjuvant compositions disclosed herein comprise influenza strains that are resistant to antiviral therapy (e.g. resistant to oseltamivir and/or zanamivir), including resistant pandemic strains.

In certain embodiments, the adjuvant compositions disclosed herein comprise a new strain compared to the hemagglutinins in currently-circulating human strains, i.e., one that has not been evident in the human population for over a decade (e.g. H2), or has not previously been seen at all in the human population (e.g. H5, H6 or H9, that have generally been found only in bird populations or H7 in swine populations). In certain embodiments, the adjuvant compositions disclosed herein comprise a strain capable of being transmitted horizontally in the human population and pathogenic to humans. In certain embodiments, the adjuvant compositions disclosed herein comprise a strain with H5 hemagglutinin type as it is preferred for immunizing against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3, with clades 1 and 3 being, particularly relevant.

In certain embodiments, the adjuvant compositions disclosed herein comprise an influenza virus strain obtained by reverse genetics techniques. Reverse genetics techniques allow influenza viruses with desired genome segments to be prepared in vitro using plasmids. Typically, it involves expressing (a) DNA molecules that encode desired viral RNA molecules e.g. from Pol1 promoters, and (b) DNA molecules that encode viral proteins e.g. from poIII promoters, such that expression of both types of DNA in a cell leads to assembly of a complete intact infectious virion. The DNA preferably provides all of the viral RNA and proteins, but it is also possible to use a helper virus to provide some of the RNA and proteins.

In certain embodiments, the adjuvant compositions disclosed herein comprise an influenza A virus may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from the A/WSN/33 virus, or from any other virus strain useful for generating reassortant viruses for vaccine preparation. Typically, the strain includes at least one RNA segment that originated in a mammalian (e.g. in a human) influenza virus. It may include NS segment that originated in an avian influenza virus.

The viruses used as the source of the antigens can be grown either on eggs or in cell culture. The current standard method for influenza virus growth uses embryonated hen eggs, with virus being purified from the allantoic fluid. Alternatively, viruses may be generated in mammalian cell culture (MDCK cells).

The method for propagating virus in cultured cells generally includes the steps of inoculating the cells with the virus strain to be cultured, cultivating the infected cells for a desired time period for virus propagation, determined by virus titer or antigen expression (e.g. between 24 and 168 hours after inoculation) and collecting the propagated virus. The cultured cells are inoculated with a virus (measured by MOI, PFU or TCID$_{50}$) to cell ratio of 1:500 to 1:1, preferably 1:100 to 1:5, more preferably 1:50 to 1:10. In certain embodiments, the MOI (multiplicity of infection) is between 0.001 to 0.1. The virus is added to a suspension of the cells or is applied to a monolayer of the cells, and the virus is absorbed on the cells for 60 minutes but usually less than 300 minutes, preferably between 90 and 240 minutes at 25° C. to 40° C., preferably 28° C. to 37° C. Typically, the virus is added to the cells for up to 60 min at room temperature or 30-45 min at 37° C. Then the inoculum is aspirated and replaced with culture medium with trypsin and the cells are followed up to 4 days for CPE.

The infected cell culture (e.g., monolayers) may be removed either by freeze-thawing or by enzymatic action to increase the viral content of the harvested culture supernatants. The virus may release from the cells (budding) with the aid of its neuraminidase wherein the cells are eventually lysed. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01, Infected cells may be harvested 30 to 60 hours post infection. Preferably, the cells are harvested 34- to 48 hours post infection. Still more preferably, the cells are harvested 38 to 40 hours post infection. Proteases (typically trypsin) are generally added during cell culture to allow viral release, and the proteases can be added at any suitable stage during the culture.

Hemagglutinin (HA) is an immunogen in inactivated influenza vaccines, and vaccine doses are typically standardized by reference to HA levels, typically as measured by a single radial immunodiffution (SRID) assay. HA used with the disclosure may be a natural HA as found in a virus, or may have been modified.

In certain embodiments, adjuvant compositions may include a detergent e.g. a polyoxyethylene sorbitan ester surfactant (known as Tweens), an octoxynol (such as octoxynol-9 (Triton X-100) or t-octylphenoxypolyethoxyethanol), a cetyl trimethyl ammonium bromide (CTAB), or sodium deoxycholate, particularly for a split or surface antigen vaccine. The detergent may be present only at trace amounts. Thus the vaccine may include less than 1 mg/ml of each of octoxynol-10, alpha-tocophetyl hydrogen succinate and polysorbate 80. Other residual components in trace amounts could be antibiotics (e.g. neomycin, kanamycin, polymyxin B).

Intradermal Administration

In certain embodiments, the disclosure contemplates intradermal administration using hypodermic injections. In certain embodiments, the disclosure contemplates intradermal administration using an intradermal adapter. Typically, the adapter functions like a sleeve, standardizing the depth and angle of the injection with a needle or syringe.

In certain embodiments, the disclosure contemplates intradermal administration using disposable-syringe jet injectors. The depth of a jet injection is determined by the pressure of the liquid stream, the diameter of the syringe orifice, or the distance of the orifice from the skin.

In certain embodiments, the disclosure contemplates intradermal administration using microneedles. Typically microneedle patches consist of micro-scale needles (100-700 microns) coated with vaccine or medication, leveraging the moisture in the skin to deliver the vaccine or pharmaceutical product directly into the intradermal layer. Hollow microneedles mounted on syringes are also contemplated which can deliver liquid or powder vaccines.

In certain embodiments, the disclosure contemplates intradermal administration using electroporation. In certain embodiments, dual-depth electroporation is configured for simultaneous intradermal and intramuscular delivery in an amount sufficient to elicit antibody and cellular immune responses.

Formulations

The compositions of the disclosure may contain adjuvants described herein can be formulated in a sufficient amount to modulate an immune response with or without an antigen. Such a formulation can be used as a therapeutic or prophylactic in the treatment of pathogens, e.g., influenza virus infection. Toxicity and therapeutic efficacy of such compounds can be determined by standard pharmaceutical procedures in cell cultures or experimental animals.

The data obtained from cell culture assays and animal studies can be used in formulating a range of dosage for use in humans. The dosage of such compounds lies preferably within a range of circulating concentrations that includes little or no toxicity. The dosage may vary within this range depending upon the dosage form employed and the route of administration utilized. A dose may be formulated in animal models to achieve a circulating plasma concentration range that provides a booster stimulus to generate a rapid viral neutralizing response as determined using standard testing protocols in animals. Such information can be used to more accurately determine useful doses in humans. Levels of the elicited antibodies in plasma may be measured, for example, by standard ELISA type assays or using other formats.

The adjuvants and antigens disclosed herein may serve the role of a prophylactic vaccine, wherein the host produces antibodies and/or cytotoxic T cell (CTL) responses against influenza virus HA protein, which then serve to neutralize influenza viruses by inhibiting further influenza infection. Administration of the compounds as a prophylactic vaccine comprise administering to a host a concentration of antigenic and adjuvant compounds effective in raising an immune response sufficient to elicit neutralizing antibody responses to influenza virus major antigenic components (HA, NA, M2), and/or virus specific CTLs which are mainly directed against epitopes of the highly conserved internal viral proteins, like M1, NP, PA and PB2 and thus inhibit the ability of the virus to infect cells. The exact concentration will depend upon the specific compound to be administered, but may be determined by using standard techniques for assaying the development of an immune response which are well known to those of ordinary skill in the art.

Qualitative and quantitative analysis of the immune response to an antigen can be conducted by any method known in the art, including, but not limited to, measuring antigen-specific antibody production, activation of specific populations of lymphocytes such as CD4+, CD8+ T cells, or NK cells, production of cytokines such as IFN-γ, IL-1β, IL-2, IL-4, IL-5, IL-10 or IL-12 and/or release of histamine. Methods for measuring specific antibody responses include enzyme-linked immunosorbent assay (ELISA), ELISpot (Enzyme-Linked ImmunoSpot), hemagglutination inhibition assay (HAI) and microneutralization assays and are well known in the art. Measurement of specific types of lymphocytes such as CD4+ T cells can be achieved, for example, with fluorescence-activated cell sorting (FACS). Serum concentrations of cytokines can be measured, for example, by ELISA. These and other assays to evaluate the immune response to an immunogen are well known in the art.

Adjuvant composition may be formulated with additional suitable adjuvants in order to enhance the immunological response. Combination adjuvants can include but not limited to, chemokines that are upregulated in the skin (IP-10, MIP-1, MCP, IFN lambda, GMCSF) with 1,8-dihydroxy-9,10-dihydroanthracen-9-one or derivative thereof, fullerene or derivatives thereof, and N-(3,5-bis-trifluoromethyl-phenyl)-5-chloro-2-hydroxy-benzamide or derivatives thereof. Other combination may include surface active substances such as lysolecithin, pluronic polyols, polyanions; other peptides; oil emulsions; and potentially useful human adjuvants such as BCG and *Corynebacterium parvum*. Adjuvants suitable for co-administration should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-1, GcMAF, B-alethine, MPC-026, Adjuvax, CpG ODN, Betafectin, and MF59 (see Kim et al., 2000, Vaccine, 18: 597).

For all such treatments described above, the exact formulation, route of administration and dosage can be chosen by the individual physician in view of the patient's condition. (See e.g., Fingl et al., 1975, in "The Pharmacological Basis of Therapeutics"). It should be noted that the attending physician would know how to and when to terminate, interrupt, or adjust administration due to toxicity, or to organ dysfunctions. Conversely, the attending physician would also know to adjust treatment to higher levels if the clinical response was not adequate (precluding toxicity). The magnitude of an administered dose in the management of the viral infection of interest will vary with the severity of the condition to be treated and the route of administration. The dose and perhaps prime-boost regimen, will also vary according to the age, weight, and response of the individual patient. A program comparable to that discussed above may be used in veterinary medicine.

Generally, the compositions of the disclosure preferably also comprise a pharmaceutically acceptable excipient, and may be in various formulations. As is well known in the art, a pharmaceutically acceptable excipient is a relatively inert substance that stabilizes and facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Generally, these compositions are formulated for administration by injection or inhalation, e.g., intraperitoneally, intravenously, subcutaneously, intradermally, intramuscularly, etc. Accordingly, these compositions may be combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, more than one antigen(s) may be present in a composition. Such compositions may contain at least one, at least two, at least three, at least four, at least five, or more different antigen(s). Such "cocktails", as they are often denoted in the art, may be particularly useful in immunizing against pathogens present in different variants.

In certain embodiments, compositions are contained within colloidal dispersion systems, such as microspheres, beads, macromolecular complexes, nanocapsules and lipid-based system, such as oil-in-water emulsions, micelles, mixed micelles and liposomes. Colloidal dispersion systems can provide effective encapsulation of linker-containing compositions. The encapsulation composition further comprises any of a wide variety of components. These include, but are not limited to, alum, lipids, phospholipids, lipid membrane structures (LMS), polyethylene glycol (PEG) and other polymers, such as polypeptides, polyvinyl alcohol, polyvinyl pyrolildone, gelatin, hyaluronic acid, other glycopeptides, polylactide/polyglycolide copolymers, and polysaccharides.

Oil-in-water emulsions are also contemplated. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter are preferred as they can be subjected to filter sterilization.

In certain embodiments, the adjuvant compositions can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice, of this disclosure. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

In certain embodiments, the adjuvant compositions comprise surfactants. Surfactants can be classified by their "HLB" (hydrophile/lipophile balance). Preferred surfactants of the disclosure have a HLB of at least 10, preferably at least 15, and more preferably at least 16. The disclosure can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate) Span 85 (sorbitan trioleate), lecithin and Triton X-100.

The adjuvant composition may include preservatives such as thimerosal or 2-phenoxyethanol.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition will generally be between 5.0 and 8.1, and more typically between 6.0 and 8.0 e.g., between 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a "multidose" kit). The inclusion of a preservative is preferred in multidose arrangements. As an alternative (or in addition) to including a preservative in multidose compositions, the compositions may be contained in a container having an aseptic adaptor for removal of material.

The antigen and adjuvant and optionally other pharmaceutical excipients in a composition will typically be in admixture, although they may initially be presented in the form of a kit of separate components for extemporaneous admixing.

EXPERIMENTAL

Anthralin as an Adjuvant for Influenza Vaccination

The efficacy of anthralin as an adjuvant for influenza vaccination was tested. Mice were intradermally vaccinated with the H3N2 subunit vaccine A/Victoria/210/2009 with or without anthralin. Anthralin was tested in 3 dilutions at 1-log differences (11.9, 119 and 1190 nanomoles). Controls for vaccine alone at the tested dose (1 µg) and at a high dose (5 µg) were used. Imiquimod is a TLR 7 agonist which is an FDA approved organic compound as a cream formulation (Aldara) for the treatment of HPV. Imiquimod dissolved in DMSO was combined with vaccine and was used as a positive control for an adjuvanted effect, which improved the longevity of immune responses and conferred complete survival of mice challenged with $4 \times LD_{50}$ of heterologous influenza virus (A/Udorn/1972, H3N2) 6 months after immunization. DMSO was used as a negative control as it was the solvent for anthralin. As shown in FIG. 1, co-administration of anthralin with the subunit influenza vaccine A/Victoria/210/2009, increased survival to 80% as compared with vaccine alone which at low or high dose partially protected the immunized groups (40 and 50% survival rates, respectively), following challenge with the influenza virus. Mice that demonstrate more than 80% survival following high lethal challenge are considered as fully protected. The adjuvanted groups of imiquimod and anthralin showed the lowest body weight loss and fewer signs of disease (FIG. 1A, B).

The mechanism of anthralin in skin has been studied extensively, but as of now has not been tested as an adjuvant for skin immunization. We have shown that anthralin can improve survival to respiratory influenza infection when used as an adjuvant for skin vaccination against influenza. At three different doses tested, anthralin showed an 80% or better survival rate, despite greater weight loss, following infection with a closely related virus, A/Udorn 1972. The mechanism of anthralin is mediated enhanced immunity is being explored, but is likely due to large amounts of IL-1 beta and TNF-α production by primary human keratinocytes (Brock, et al. Unpublished). Additionally, our preliminary data show that anthralin differentially modulates cell-signaling pathways downstream of TLR3, these cytokines are likely mediated through inflammasome activation independent of NLRP3 activation as caspase-1 is not activated. Therefore, we hypothesize that anthralin is mediating its effect as a skin adjuvant by mediating keratinocyte cell death independent of caspase-1 activation.

IMD 0354 as an Adjuvant for Influenza Vaccination

Mice were intradermally vaccinated with the subunit vaccine A/Victoria/210/2009 with or without IMD 0354. Controls were used for vaccine alone at the tested dose (1 μg) and at a high dose (5 μg). Imiquimod, which is a TLR 7 agonist, combined with vaccine and used as a positive control for an adjuvant effect, which improved survival of these mice over vaccine alone at low or high dose. DMSO was use as a negative control as it is the solvent for IMD 0354. As shown in FIG. 2, co-administration of IMD 0354 with the subunit influenza vaccine A/Victoria/210/2009, conferred 100% survival as compared with vaccine alone following 4×$LD_{50}$ challenge with, A/Udorn/1972 (H3N2 subtype) with minimal body weight loss as compared to all vaccinated groups (FIG. 2A, B). These results clearly show that as an adjuvant for influenza vaccination IMD 0354 improved protective immunity to influenza. These data challenge the current role of IMD 0354 as immunosuppressive, but IMD has never been used as an adjuvant for vaccination. IMD 0354 also modulated IgG subclass expression in a time-dependent manner. Serum IgG2a was increased in mice after intradermal vaccination with A/Victoria/210/2009, indicating a role for antibody-dependent cell cytotoxicity (ADCC) in the enhanced survival mediated by IMD 0354 as shown in FIG. 2C.

Pristine Fullerene C60 as an Adjuvant for Influenza Vaccination

Mice were intradermally vaccinated with the subunit vaccine A/Victoria/210/2009 with or without fullerene. Controls were used for vaccine alone at the tested dose (1 μg) and at a high dose (5 μg). Imiquimod, which is a TLR 7 agonist, combined with vaccine was used as a positive control for an adjuvant effect, which improved survival of these mice when compared to vaccine alone. As shown in FIG. 3, co-administration of fullerene with the subunit influenza vaccine A/Victoria/210/2009, increased survival to 80% as compared to 40% survival with vaccine alone at low dose or vaccine alone at high dose (50%), following challenge with the influenza virus A/Udorn/1972 (H3N2 subtype) (FIG. 3A, B).

The invention claimed is:

1. A method of pathogenic immunization comprising administering to skin an effective amount of an antigen or vaccine and an adjuvant to a subject in need thereof, wherein adjuvant is 1,8-dihydroxy-9,10-dihydroanthracen-9-one.

2. The method of claim 1, wherein the antigen comprises a polypeptide sequence of a pathogen.

3. The method of claim 2, wherein the pathogen is a virus, bacteria, or fungus.

4. The method of claim 1, wherein the antigen is a virus particle, viral envelope protein, an influenza hemagglutinin or neuraminidase.

5. The method of claim 1, wherein the vaccine is a live, attenuated, or killed virus.

6. The method of claim 1, wherein administration to skin is topical administration or intradermal administration.

7. The method of claim 1, wherein administration to skin is by syringe or microneedle.

8. A method of pathogenic immunization comprising administering to skin an effective amount of an antigen or vaccine and an adjuvant to a subject in need thereof, wherein adjuvant is N-(3,5-bis-trifluoromethyl-phenyl)-5-chloro-2-hydroxy-benzamide.

9. The method of claim 8, wherein the antigen comprises a polypeptide sequence of a pathogen.

10. The method of claim 9, wherein the pathogen is a virus, bacteria, or fungus.

11. The method of claim 8, wherein the antigen is a virus particle, viral envelope protein, an influenza hemagglutinin or neuraminidase.

12. The method of claim 8, wherein the vaccine is a live, attenuated, or killed virus.

13. The method of claim 8, wherein administration to skin is topical administration or intradermal administration.

14. The method of claim 8, wherein administration to skin is by syringe or microneedle.

* * * * *